United States Patent [19]

Shutske

[11] Patent Number: 4,871,764

[45] Date of Patent: Oct. 3, 1989

[54] 12-HALOGENATED FORSKOLIN DERIVATIVES

[75] Inventor: Gregory M. Shutske, Somerset, N.J.

[73] Assignee: Hoechst-Roussel Pharmaceuticals, Inc., Somerville, N.J.

[21] Appl. No.: 932,553

[22] Filed: Nov. 20, 1986

[51] Int. Cl.$^4$ .................... A61K 31/35; C07D 311/92
[52] U.S. Cl. .................................... 514/455; 549/389; 514/913
[58] Field of Search ................ 549/389; 514/455, 913

[56] References Cited

U.S. PATENT DOCUMENTS

| | | | |
|---|---|---|---|
| 4,134,986 | 1/1979 | Bajwa et al. | 514/455 |
| 4,476,140 | 10/1984 | Sears et al. | 514/455 |
| 4,517,200 | 5/1985 | Kreutner et al. | 514/455 |
| 4,639,443 | 1/1987 | Kosley, Jr. et al. | 544/121 X |
| 4,639,446 | 1/1987 | Kosley, Jr. et al. | 514/455 X |
| 4,677,103 | 6/1987 | Kosley, Jr. et al. | 549/229 X |

FOREIGN PATENT DOCUMENTS 3346869  12/1984  Fed. Rep. of Germany .

OTHER PUBLICATIONS

Caprioli et al., "Forskolio Lowers Intraocular Pressure by Reducing Aqueous Inflow" in *Invest. Ophthalmol. Vis. Sci.*, 25, 268, (1984).

*Primary Examiner*—John W. Rollins
*Assistant Examiner*—Wendy Catchpole
*Attorney, Agent, or Firm*—Tatsuya Ikeda

[57] ABSTRACT

Novel 12-halogenated forskolin derivatives, intermediates and processes for their preparation, and methods for reducing intraocular pressure utilizing the compounds or compositions are disclosed.

26 Claims, No Drawings

12-HALOGENATED FORSKOLIN DERIVATIVES

The present invention relates to 12-halogenated forskolin derivatives of Formula 1

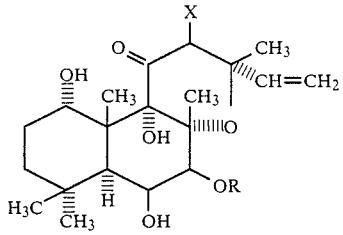

wherein X is F, Cl, Br and I; R is hydrogen,

wherein $R_1$ is hydrogen or lower alkyl,

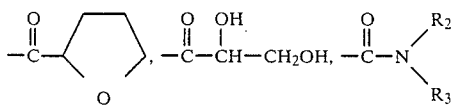

where $R_2$, $R_3$ are the same or different and are H or lower alkyl; the optical and geometric isomers thereof, which are useful for reducing intraocular pressure, alone or in combination with inert adjuvants.

The present invention also relates to compounds of the formula 2,

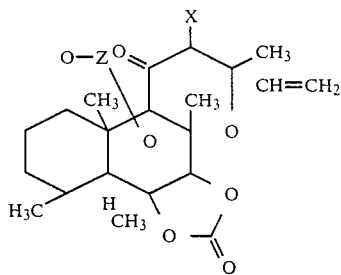

wherein X is as previously defined and Z is either

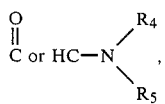

where $R_4$, $R_5$ are the same or different and are hydrogen or lower alkyl; or the optical and geometric isomers thereof, which are useful as intermediates for the preparation of the 12-halogenated forskolin derivatives of the present invention.

As used throughout the specification and appended claims, the term "alkyl" refers to a straight or branched chain hydrocarbon radical containing no unsaturation, such as methyl, ethyl, 1-propyl, 2-propyl, 2-methylpropyl, 1-pentyl, 3-hexyl, and the like. The term "alkanoyl" refers to a monovalent substituent which consists of an alkyl group linked through a carbonyl group having its free valence bond from the carbon of the carbonyl group

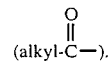

Examples of alkanoyl groups are formyl, acetyl, propionyl, 2,2-dimethylacetyl, hexanoyl, and the like. The term "lower" as applied to any of the aforementioned groups refers to an alkyl group having a carbon skeleton containing up to and including 6 carbon atoms.

In the formulas presented herein the various substituents are illustrated as joined to the nucleus (labdane structure) by one of two notions: a solid line (———) indicating a substituent which is in the β-orientation, (i.e., above the plane of the molecule) and a broken line (----) indicating a substituent which is in the α-orientation (i.e., below the plane of the molecule). The formulae have all been drawn to show the compounds in their absolute stereochemical configuration. Inasmuch as the starting materials having such labdane nucleus are naturally occurring or are derived from naturally occurring materials, they, as well as the final products, have a labdane nucleus existing in the single absolute configuration depicted herein. The processes of the present invention, however, are intended to apply as well to the synthesis of the labdanes of the racemic series.

In addition to the optical centers of the labdane nucleus, the substituents thereon may also contain chiral centers contributing to the optical properties of the compounds of the present invention and providing a means for the resolution thereof by conventional methods, for example, by the use of optically active acids. A wavy line ( ~ ) connecting a group to a chiral center indicates that the stereochemistry of the center is unknown, i.e. the group may exist in any of the possible orientations. The present invention comprehends all optical isomers and racemic forms of the compounds of the present invention, where such compounds have chiral centers in addition to those of the labdane nucleus.

the novel 12-halogenated forskolin derivatives of the present invention are synthesized by the processes illustrated in the Reaction Schemes A and B, wherein the groups R, $R_1$ through $R_5$ are as previously defined.

To prepare a basic labdane 4, a 1α, a 9α-dihydroxylabdane 3 where $R_6$ is lower alkanoyl is condensed with a formamide dialkylacetal of the formula 11,

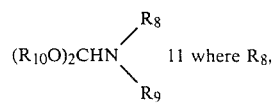

$R_9$ and $R_{10}$ are independently lower alkyl, or $R_8$ and $R_9$ taken together with the nitrogen atom to which they are attached form a group of the formula

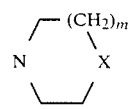

where X is $CHR_{11}$ wherein $R_{11}$ is hydrogen, lower alkyl or a group of the formula $OR_{12}$ where $R_{12}$ is hydrogen, lower alkyl or a group of the formula $COR_{13}$ wherein $R_{13}$ is lower alkyl and m is 0 or 1. The condensation is preferably performed in the absence of an added solvent, excess formamide dialkylacetal serving both as the reactant and solvent. A dipolar aprotic solvent such as dimethylformamide, dimethylacetamide, hexamethylphosphoramide or dimethylsulfoxide may be employed, however, as the reaction medium. The temperature at which the condensation is conducted is not critical. A condensation temperature within the range of about 25° to about 100° C. is generally employed to assure a reasonable rate of reaction. A temperature of about 45° to about 65° C. is preferred.

To furnish a basic labdane of formula 5 wherein $R_8$ and $R_9$ are as above, a 7 β-alkanoyloxy-6β-hydroxylabdane 4 is hydrolyzed to the 6β, 7β-dihydroxylabdane 5. The hydrolysis is carried out in an aqueous alkanol such as aqueous methanol, ethanol, 1- or 2-propanol or t-butanol, aqueous methanol being preferred, containing an alkali carbonate such as lithium, sodium or potassium carbonte, potassium carbonate being preferred, at a hydrolysis temperature within the range of about 10° to about 75° C., a hydrolysis temperature of about 25° C. being preferred.

To introduce a 6β,7β-carbonate function into the basic labdane nucleus, i.e., to prepare a compound of formula 6, a 6β,7β-dihydroxylabdane of formula 5 is treated with a compound of formula 12.

wherein Hal is bromo or chloro, preferably chloro, in the presence of an organic base such as trimethyl- or triethylamine, pyridine, lutidine or collidine at a reduced temperature within the range of about −24° to about 25° C. The preferred organic base is pyridine and the preferred reaction temperature is about 0° C.

Alternatively labdane 6 can be prepared by treating the 6β,7β-dihydroxylabdane 5 with a compound of the formula

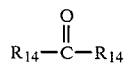

where $R_{14}$ is imidazole,

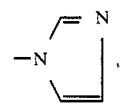

in the presence of an organic base such as trimethyl or triethylamine, diisopropyl-ethylamine, etc., at a temperature ranging from 25° to 150 ° C. for a time period of 30 to 120 minutes.

Labdane 6 is treated with a silyl halide of the formula 13

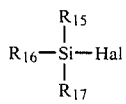

where $R_{15}$, $R_{16}$, $R_{17}$ are independently lower alkyl and Hal is a halogen, preferably Cl, in the presence of a base such as potassium hydride, lithium diisopropylamide or, preferably, lithium bis[trimethylsilyl]amide to form labdane 7. Typically this reaction is carried out in the presence of an aprotic solvent, e.g. tetrahydrofuran, diethyl ether, dimethoxy ethane, tolune, etc., at a temperature of −25° to 25° C. for a period of time of from 1 to 3 hours.

To introduce a halogen group at the 12 position, labdane 7 is reacted in a conventional manner with a N-halosuccinimide such as N-bromo-, N-chloro-, N-iodosuccinimide, etc., or other standard suitable halogenating agents such as N-halophthalimide or N-halocarprolactam, under the influence of flouride ion. Tetramethylammonium fluoride, tetraethylammonium flouride, benzyltrimethylammonium fluoride and potassium fluoride dicyclohexyl-18-crown-6 are suitable sources of fluoride ion, with tetra-n-butylammonium fluoride being preferred. Typically when using N-halosuccinimide, the reaction is carried out in a polar aprotic solvent, e.g. diethyl ether, tetrahydrofuran, or dimethoxy ethane at a temperature of −65° to 0° C. for a time period of 5 to 60 minutes to form labdane 8, where Hal is a halogen (cl, Br, or I).

The removal of the 6β,7βcarbonate function is achieved by hydrolyzing compound 8 by conventional means. Typically compound 8 is treated with a basic material, e.g. $K_2CO_3$, $Li_2CO_3$, $Na_2CO_3$, etc., in the presence of water and a miscible organic solvent, e.g. methanol, ethanol, dioxane, tetrahydrofuran, etc., at a temperature ranging from 25° to 60° C. for a time period of 1 to 8 hours in order to form compound 9.

Compound 9 is then subjected to hydrolysis under acidic conditions to form 12-halogenated desacetyl forskolin of the invention of the formula 10. Typically this hydrolysis is carried out in the presence of an organic acid e.g. acetic acid, citric acid, oxalic acid, etc., in water and a miscible organic solvent, e.g. methanol, ethanol, dioxane, tetrahydrofuran, etc. at temperature of 0° to 60° C. for a time period of 1 to 36 hours to obtain compount 10.

In an alternative procedure, (Reaction Scheme B) a dicarbonate labdane of the formula 14 is selected. Such labdanes are known in the art or can be synthesized utilizing conventional techniques. In this regard, reference is made to S.V. Bhat et. al., *J. Chemical Society* 1982, 767. Labdane 14 is then reacted with the silyl halide 13, in the same manner previously described for reaction of compound 6, to form labdane 15 having a silyl ether group where $R_{15}$, $R_{16}$, and $R_{17}$ are as previously defined.

The introduction of a halogen group at the 12-position of labdane 15 is carried out in the same manner as previously described for the formation of compound 8 from compound 7 except that the halogen group is restricted to F and Cl, to form labdane 16, where Hal is F or Cl.

For the case where Hal is F, labdane 14 is treated with a base, as previously described for the synthesis of labdane 7, and then allowed to react with acetyl hypofluorite. Acetyl hypofluorite is generated from dilute fluorine in nitrogen and sodium acetate, as described by Rozen and Brand, Synthesis 1985, 665.

The resulting dicarbonate 16 is removed by subjecting labdane 16 to basic hydrolysis. Typically this is carried out, as previously described, with an inorganic base, e.g. $K_2CO_3$, $Li_2CO_3$, $Na_2C_3$, etc., in the presence of water and a miscible solvent, e.g. methanol, ethanol, dioxane, etc., at a temperature ranging from 25° to 60°

C. for a time period of 1 to 8 hours in order to form compound 10 where Hal is F or Cl.

The dicarbonate can be removed in two steps by subjecting labdane 16 to mild basic hydrolysis. Typically this is carried out with an inorganic base, e.g. NaHCO$_3$ or KHCO$_3$ in the presence of water and a miscible solvent e.g. methanol, ethanol, dioxane, tetrahydrofuran, etc. at a temperature ranging from 10° to 35° C. for a time period of 6-24 hours in order to form compound 17 where Hal is F or Cl. Labdane 10 can then be obtained from 17 by the conditions described above.

To form compound 1 of the invention where R is

compound 10 is reacted under standard acylating conditions. Typically compound 10 is reacted with an acylating agent, e.g. anhydrides, (R$_1$C)$_2$), or acid halides,

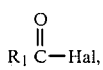

where Hal is a halogen such as Cl, Br, etc., in the presence of a basic solvent such as pyridine, collidine, lutidine, triethylamine etc., at a temperature of 0° to 30° C. for a time period ranging from 1 to 24 hours.

To form compound 1 of the invention where R is

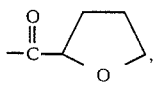

compound 10 is reacted with tetrahydrofuroic acid,

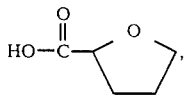

in the presence of 1,3-dicyclohexylcarbodiimide and 4-dimethylaminopyridine in an inert solvent such as methylene choloride, chloroform benzene or toluene at a temperature of 0° to 30° C. for a time period of 1 to 24 hours.

To form compound 1 of the invention where R is

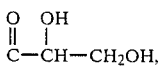

compound 10 is reacted with potassium (2,2-dimethyl-1,3-dioxolano-4yl)oate in the presence of 1,3-dicyclohexylcarbodiimide and 4-dimethylaminopyridine hydrochloride in an inert solvent such as methylene chloride, chloroform, benzene or toluene of a temperature of 0° to 30° C. for a time period of 1 to 24 hours. The resulting intermediate is then subjected to hydrolysis under acidic conditions, typically in the presence of an organic acid e.g. acetic acid, citric acid, oxalic acid, etc. in water and a miscible organic solvent e.g., methanol, ethanol, dioxane, tetrahydrofuran, etc. at a temperature of 0° to 60° for a time period of 1 to 72 hours.

To form compound 1 of the invention where R is

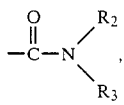

compound 10 is reacted with an isocyanate of the formula R$_2$N=C=O or a carbamoyl chloride of the formula

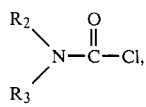

in the presence of an organic base such as lithium diisopropylamide or, preferably, lithium bis[trimethylsilyl]amide in a polar aprotic solvent, e.g. tetrahydrofuran, diethyl ether, dimethoxyethane, etc. at a temperature of 0° to 100° C. for a time period of 1 to 24 hours.

The labdane starting materials for the processes of the present invention, i.e., labdanes of formula 3 and 14 wherein R$_6$ is hydrogen or acyl, as described in U.S. Pat. No. 4,134,986, issued Jan. 16, 1979 to B.S. Bajwa, et. al. or may be prepared from compounds disclosed therein by conventional processes.

The labdanes of the present invention are useful in the treatment of elevated intraocular pressure by virtue of their ability to reduce intraocular pressure as determined by the method described by J. Caprioli, et al., Invest. Ophthalmol. Vis. Sci., 25, 268 (1984). The results of the determination expressed as percent decrease of outflow pressure is presented in the Table.

TABLE

| COMPOUND | CONCENTRATION (%) | DECREASE IN OUTFLOW PRESSURE (%) |
|---|---|---|
| 12-chlorodesacetyl forskolin | 2 | 22 |
| 12-chloroforskolin hemihydrate | 2 | 35 |
| 12-bromodesacetyl forskolin | 2 | 37 |
| 12-bromo-7-(2-tetrahydrofuranoyl)desacetyl forskolin | 1 | 16 |
| 12-bromo-7-(2,3-dihydroxypropionyl)-desacetyl forskolin | 0.25 | 28 |
| Forskolin (standard) | 0.25 | 66 |

Intraocular pressure reduction is achieved when the present labdanes are administered to a subject requiring treatment as an effective topical dose of a 0.01 to 3.0% solution or suspension. A particularly effective amount is about 3 drops of a 1% preparation per day. It is to be understood, however, that for any particular subject, specific dosage regimens should be adjusted according to the individual need and the professional judement of the person administering or supervising the administration of the aforesaid compound. It is to be further understood that the dosages set forth herein are exemplary only and that they do not, to any extent, limit the scope or practice of the invention.

Effective amounts of the compounds of the present invention may be administered to a subject by any one of various methods, for exampy, orally as in capsules or tablets, parenterally in the form of sterile solutions or suspensions, in some cases intravenously in the form of sterile solutions, or suspensions, and topically in the form of solutions, suspension or ointments, and by aerosol spray.

Effective quantities of the compounds of the invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 0.3-30 milligrams of the active compound.

The tablets, pills, capsules, troches and the like may also contain the following ingredients: a binder such as microcrystalline cellulose, gum tragancanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purpose of parenteral or topical therapeutic administration, the active compounds of the invention may be incorporated into a solution, suspension, ointment or cream. These preparations should contain at least 0.01% of active compound, but may be varied between 0.5 and about 5% of the weight thereof. The amount of active compounds in such compositions is such that a suitable dosage will be obtained. Preferred compositions and preparations according to the present invention are prepared so that a parenteral dosage unit contains between 0.01 to 10 milligrams of active compound.

The solutions or suspensions for topical or parenteral administration may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetra-acetic acid; buffers such as acetates, citrates or phosphates and agents for the adjustment of tonicity such as sodium chloride or dextrose. The parenteral preparation can be enclosed in ampules or disposable syringes; the topical preparation may be enclosed in multiple dose vials or dropping bottles, made of glass or plastic.

The following examples are for illustration purposes only and are not to be construed as limiting the invention. All temperatures are given in degrees Centigrade.

EXAMPLE 1

(a) Desacetylforskolin 1,9:6,7-Dicarbonate 11,12-Enol-t-butyl-dimethylsilyl ether Forskolin 1,9:6,7-dicarbonate (1.1846 g. 2.82 mmole) was dissolved in 25 ml of dry tetrahydrofuran (THF) and t-butyldimethylsilyl chloride (0.64 g. 4.27 mmole) was added, followed by 3.3 mil of 1M lithium bis(trimethylsily)amide (3.3 mmole). The reaction was complete after 1 hour. The reaction mixture was distributed between aqueous $NaHCO_3$ solution and ether and then the organic phase was dried and evaporated. The residue was triturated well with pentane, giving 1.1288 g (75%) of desacetylforskolin 1,9:6,7-dicarbonate 11,12-enol-t-butyldimethylsilyl ether, mp 175–177° C.

| ANALYSIS: | | |
|---|---|---|
| Calculated for $C_{28}H_4O_8Si$: | 62.89% C | 7.92% H |
| Found: | 63.18% C | 7.86% H |

(b) 12-Chlorodesacetylforskolin 1,9:6,7-Dicarbonate

Desacetylforskolin 1,9:6,7-dicarbonate 11,12-enol-t-butyldimethylsilyl ether of Example 1(a) (0.294 g, 0.550 mmole) was dissolved in 10 ml of dry THF and chilled to −75° C. N-chlorosuccinimide (0.080 g, 0.60 mmole) was added in 2 ml of THF and then 0.60 ml of 1M tetra-n-butylammonium fluoride (0.60 mmole) was added dropwise. After 15 minutes the reaction mixture was evaporated and applied directly to a flash column (5% ethyl acetate-$CH_2Cl_2$). Evaporation of the product-containing fractions gave 0.1546 g (62%) of product. Recrystallization from benzene-pentane yielded 12-chlorodesacetylforskolin 1,9:6,7-dicarbonate, mp 165° (decomp).

| ANALYSIS: | | |
|---|---|---|
| Calculated for $C_{22}H_{28}ClO_8$: | 58.08% C | 5.98% H |
| Found: | 57.89% C | 6.00% H |

(c) 12-Chlorodesacetylforskolin

12-Chlorodesactylforskolin 1,9:6,7-dicarbonate of Example 1(b) (0.1777 g, 0.391 mmole) was stirred for 5 hours in 10 ml of $K_2CO_3$/methanol/$H_2O$. The reaction mixture was distributed between ether and $H_2O$ and then the organic phase was separated and dried. The crude reaction product was purified by flash chromatography (30% ethyl acetate-hexane) to give 0.0665 g of pure product (42%). Recrystallization from $CH_2Cl_1$-pentane yielded 12-chlorodesacetylforskolin, mp 175°–177° C.

| ANALYSIS: | | |
|---|---|---|
| Calculated for $C_{20}H_{21}ClO_6$: | 59.62% C | 7.76% H |
| Found: | 59.47% C | 7.96% H |

EXAMPLE 2

12-Chloroforskolin Hemihydrate

12-Chlorodesacetylforskolin of Example 1(c) (0.140 g, 0.347 mmole) was dissolved in 1.5 ml of pyridine to which 0.047 ml of acetic anhydride (0.50 mmole) was then added. The reaction mixture was stirred overnight (about 16 hours) and then distributed between H$_2$O and ether. The aqueous was separated and the organic phase was washed twice with H$_2$O and once with 5% aqueous HCl. The organic phase was then dried, evaporated and purified by flash chromatography (5% ethyl acetate CH$_2$Cl$_2$) to give 0.0717 g (46%) of 12-chloroforskolin hemihydrate. This product was combined with the product of another run and recrystallized together from CH$_2$Cl$_1$-pentane to give analytically pure material, mp 224°–226° C.

| ANALYSIS: | | |
|---|---|---|
| Calculated for C$_{22}$H$_{23}$ClO$_7$.0.5H$_2$O: | 58.20% C | 7.55% H |
| Found: | 58.14% C | 7.48% H |

EXAMPLE 3

12-Chloro-7-(2-tetrahydrofuranoyl)desacetylforskolin

12-Chlorodesacetylforskolin (0.1700 g, 0.67 mmole) of Example 1(c) was dissolved in 5 ml of CH$_2$Cl$_2$ and then tetrahydrofuroic acid (0.092 g, 0.80 mole), dicyclohexylcarbodiimide (0.144 g, 0.70 mmole) and 4-dimethylaminopyridine (0.144 g, 0.70 mmole) was added sequentially. The reaction mixture was stirred overnight (about 16 hours) and then ether was added and the resulting dicyclohexyl urea was filtered off. The residue was purified by flash chromatography (5% ethyl acetate-CH$_2$Cl$_2$) and the product-containing fractions were evaporated and the residue recrystallized from benzene-pentane to give 0.0851 g (25%) of 12-chloro-7-(2-tetrahydrofuranyl) desacetylforskolin.

| ANALYSIS: | | |
|---|---|---|
| Calculated for C$_{25}$H$_{37}$ClO$_8$: | 59.93% C | 7.44% H |
| Found: | 59.55% C | 7.35% H |

EXAMPLE 4

(a) Forskolin 1,9-dimethylformamide acetal

Forskolin (100 mg) was dissolved in 1 ml of dimethylformamide dimethylacetal. The mixture was stirred 1 hour at room temperature and overnight at 55° under nitrogen. The mixture was dissolved in ether, washed with water, dried over anhydrous sodium sulfate, filtered and concentrated to an oil. The oil was dissolved in a minimum volume of dichloromethane and chromatographed using 10 g of silica gel (230–400 mesh). Eluant: 8×3 ml of dichloromethane, 8×3 ml of 3% methanol/dichloromethane and 8×3 ml of 5% methanol/dichloromethane. Evaporation of the appropriate fractions followed by drying at 60° C. (1 mm) provided 90 mg (79.1%) of forskolin 1,9-dimethylformamide acetal as an oil.

| ANALYSIS: | | | |
|---|---|---|---|
| Calculated for C$_{25}$H$_{39}$NO$_7$: | 64.49% C | 8.44% H | 3.01% N |
| Found: | 64.69% C | 8.25% H | 3.09% N |

(b) Desacetylforskolin 1,9-dimethylformamide acetal

A solution of 225 mg of forskolin 1,9-dimethylformamide acetal of Example 4(a) was stirred at room temperature under nitrogen for 5 hours in 5 ml of saturated K$_2$CO$_3$ solution in 20% aqueous methanol. The solution was diluted with water and extracted twice with ether. The ether extractions were washed twice with water and dried over anhydrous sodium sulfate. Filtration followed by evaporation provided an oil which crystalized on standing. The crystals were dried at 113° (1 mm) to yield 192 mg, (88.5%) of desacetylforskolin 1,9-dimethylformamide acetal, mp 136°–144° C.

| ANALYSIS: | | | |
|---|---|---|---|
| Calculated for C$_{23}$H$_{37}$NO$_6$: | 65.22% C | 8.81% H | 3.31% N |
| Found: | 65.18% C | 8.76% H | 3.25% N |

(c) Desacetylforskolin 6,7-Carbonate 1,9-Dimethylformamide Acetal

Desacetylforskolin 1,9-dimethylformamide acetal (1,058 g, 2.5 mmole) of Example 4(b) was refluxed in 25 ml of toluene containing 0.50 g of N,N'-carbonyldiimidazole (3.08 mmole) and 0.55 ml of triethylamine (4.0 mmole). After 3 hours, thin layer chromatography (TLC) showed conversion to one main new product. The reaction mixture was evaporated and applied directly to a flash column. Elution with 50% ethyl acetate-hexane gave 0.976 g (87%) of product after combination of the appropriate fractions. Analytically pure desacetylforskolin 6,7-carbonate 1,9-dimethylformamide acetal was obtained by recrystallization from hexane, mp 138°–140° C.

| ANALYSIS: | | | |
|---|---|---|---|
| Calculated for C$_{24}$H$_{25}$NO$_7$: | 64.12% C | 7.85% H | 3.12% N |
| Found: | 63.91% C | 7.98% H | 3.08% N |

(d) 12-Bromodesacetylforskolin 6,7-Carbonate 1,9-dimethylformamide Acetal

Desacetylforskolin 6,7-carbonate 1,9-dimethylformamide acetal of Example 4(c) (0.450 g, 1.0 mmole) was dissolved in 10 ml. of dry THF and t-butyldimethylsilyl chloride (0.20 g, 1.3 mmole) and 1M lithium bis(trimethylsilyl)amide (1.5 ml, 1.5 mmole) were added. After 30 minutes at room temperature the reaction was distributed between NaHCO$_3$ solution and the organic phase was separated and dried. Evaporation gave an oil that resisted crystallization, and was used in the next step without further purification. The NMR (CDCl$_3$) was consistent with the formation of 12-bromodesacetyl forskolin-6,7-carbonate 1,9-dimethylformamide 11,12-enol-t-butyldimethylsilyl ether. The silyl enol ether was dissolved in 10 ml of dry THF and chilled to −65° C. N-Bromosuccinimide (0.20 g, 1.12 mmole) was then added, followed by 1.1 ml of 1M tetra-n-butylammonium fluoride (1.1 mmole). After 15 minutes the reaction mixture was evaporated and applied directly to a silica gel column. Elution with 5% ethyl acetate-CH₂Cl₂ gave 0.3718 g (70% for two steps) of product after evaporation of the appropriate fractions. Analytically pure 12-bromodesacetylforskolin 6,7-carbonate 1,9-dimethylformamide acetal was obtained by recrystallization from benzene-pentane, mp 157°–159° C.

| ANALYSIS: | | | |
|---|---|---|---|
| Calculated for $C_{24}H_{34}BrNO_7$: | 54.55% C | 6.49% H | 2.65% N |
| Found: | 54.35% C | 6.50% H | 2.41% N |

(e) 12-Bromodesacetylforskolin 1,9-dimethylformamide Acetal

12-Bromodesacetylforskolin 6,7-carbonate 1,9-dimethylformamide acetal of Example 4(d) (0.2831 g, 0.536 mmole) was stirred for 2 hours in 5 ml of methanol/H₂0/K₂CO₃. At the end of this time the reaction mixture was poured into H₂O and the pH was carefully adjusted to 6–7. The product was extracted into CH₂Cl₂, evaporated to an oil and purified by flash chromatography (10% ethyl acetate-CH₂Cl₂). Evaporation of the appropriate fractions gave 0.1885 g of a foam (70%) of 12-bromodesacetylforskolin 1,9-dimethylformamide acetal, mp 85°–87° C.

| ANALYSIS: | | | |
|---|---|---|---|
| Calculated for $C_{23}H_{36}BrNO_6$: | 54.98% C | 7.22% H | 2.79% N |
| Found: | 55.05% C | 7.42% H | 2.55% N |

(f) 12-Bromodesacetylforskolin

12-Bromodesacetylforskolin 1,9-dimethylformamide acetal of Example 4(e) (0.5187 g, 1.03 mmole) was stirred overnight (about 16 hours) in 25 ml of 1:1 methanol-80% acetic acid. The reaction mixture was then evaporated and the residue distributed between ether and NaHCO₃ solution. The organic phase was separated, dried, and evaporated and then purified by flash chromatography (30% ethyl acetate-CH₂Cl₂) to give, after evaporating the appropriate fractions, 0.4441 g (96%) of chromatographically pure product. Recrystallization from CH₂Cl₂ yielded analytically pure 12-bromodesacetylforskolin, mp 133°–135° C. (decomp).

| ANALYSIS: | | |
|---|---|---|
| Calculated for $C_{20}H_{31}BrO_6$: | 53.69% C | 6.99% H |
| Found: | 53.80% C | 7.11% H |

12-Bromoforskolin

12-Bromodesacetylforskolin (0.2448 g, 0.547 mmole) of Example 4(f) was dissolved in 5 ml of pyridine and then 0.075 ml of acetic anhydride (0.79 mmole) was added. The reaction mixture was stirred for 3 days and then evaporated and distributed between ether and 5% HCl. The organic layer was separated, dried, evaporated and purified by flash chromatography (10% ethyl acetate CH₂Cl₂) to give 0.1475 g (55%) of product. Analytically pure 12-bromodesacetylforskolin was obtained by recrystallization from benzene-pentane, mp 203° (d).

| ANALYSIS: | | |
|---|---|---|
| Calculated for $C_{22}H_{33}BrO_7$: | 53.99% C | 6.80% H |
| Found: | 53.86% C | 6.82% H |

EXAMPLE 6

12-Bromo-7-(2-tetrahydrofuranoyl)desacetyl forskolin

12-Bromodesacetyl forskolin (0.2678 g, 0.60 mmole) of Example 4(f) was dissolved in 5 ml CH₂Cl₂ containing 0.120 g (1.02 mmole) of tetrahydrofuroic acid. Dicyclohexylcarbodiimide was added (0.144 g, 0.70 mmole), followed by 4-dimethylaminopyridine (0.085 g, 0.70 mmole) and the reaction mixture was allowed to stir overnight. It was then diluted with ether and filtered through celite. Evaporation gave a gummy residue that was purified by flash chromatography (10% ethyl acetate-CH₂Cl₂) to give a mixture of diastereomers, after combining and evaporating the appropriate fractions. Recrystallization from benzene-pentane gave 0.136 g of analytically pure 12-bromo-7-(tetrahydrofurano-2-yl)desacetyl forskolin (42%), mp 203° C. (d).

| ANALYSIS: | | |
|---|---|---|
| Calculated for $C_{25}H_{37}BrO_8$: | 55.04% C | 6.84% H |
| Found: | 54.93% C | 6.81% H |

EXAMPLE 7

12 Bromo-7-(2,2dimethyl-1,3-dioxolano-4yl)desacetylforskolin

12-Bromodesacetylforskolin (0.680 g, 1.52 mmole) of Example 4(f) was dissolved in 10 ml of CH₂Cl₂. To the solution was added sequentially potassium (2,2-dimethyl-1,3-dioxolano4-yl)oate (0.313 g, 1.70 mmole), 4-dimethylaminopyridine hydrochloride (0.270 g, 1.70 mmole) and dicyclohexylcarbodinide (0.351 g, 1.70 mmole). The reaction mixture was stirred overnight and then ether was added and the precipitated urea filtered off. The filtrate was evaporated and the residue purified by flash chromatography (10% ethyl acetate-CH₂Cl₂) to give, after evaporation of the appropriate fractions and scrupulous drying (80° C., 0.1 mm Hg), 0.4217 g (48.9%) of analytically pure 12-bromo-7-(2,2-dimethyl-1,3-dioxolane-4-yl)desacetylforskolin, m.p. 115°–120° C.

| ANALYSIS: | | |
|---|---|---|
| Calculated for $C_{26}H_{39}BrO_9$: | 54.26% C | 6.83% H |
| Found: | 54.25% C | 6.85% H |

EXAMPLE 8

12-Chlorodesacetylforskolin 1,9-dimethylformamide acetal

Desacetylforskolin 6,7-carbonate 1,9-dimethylformamide acetal of Example 4(c) (1.80 g, 4.0 mmole) was dissolved in 40 ml of dry THF to which was then added 0.80 g of t-butyldimethylsilyl chloride (5.31 mmole) followed by 6.0 ml of 1M lithium bis(trimethylsilyl)amide in hexanes. This reaction mixture was stirred for 1 hour at which time TLC showed good conversion to the corresponding enol silyl ether. The reaction mixture was then distributed between ether and NaHCO$_3$ solution, after which the organic phase was separated, dried and evaporated. The residual oil was dissolved in 30 ml of dry THF which was then chilled to −65° C. N-chlorosuccinimide was then added (0.60 g, 4.50 mmole), followed by 5.0 ml of 1M tetra-n-butylammonium fluoride in THF. After 30 minutes at this temperature the reaction mixture was evaporated and applied directly to a column of 230–400 mesh silica gel, and eluting with 10% ethyl acetate-CH$_2$Cl$_2$. The product containing fractions were evaporated and shown to contain an unseparated impurity by NMR, so this material was taken on to the next step without further purification. It was hydrolyzed in 10 ml of K$_2$CO$_3$/methanol/H$_2$0 for 4 hours and then the reaction mixture was distributed between H$_2$O and ether. Evaporation and purification by flash chromatography (10% ethyl acetate-CH$_2$Cl$_2$) gave 0.4825 g of 12-chlorodesacetylforskolin 1,9-dimethylformamide acetal, m.p. 80°–85° C., after rigorous removal of the solvents at 0.1 mm Hg (26% for the three steps).

| ANALYSIS: | | | |
|---|---|---|---|
| Calculated for C$_{23}$H$_{36}$ClNO$_6$: | 60.31% C | 7.92% H | 3.06% N |
| Found: | 60.61% C | 7.99% H | 2.68% N |

It is anticipated that the resultant 12-chlorodesacetylforskolin 1,9-dimethylformamide acetal can be employed, using analogous procedures to those of Example 4(f), to obtain 12-chlorodesacetylforskolin.

EXAMPLE 9

12-Chlorodesacetylforskolin 6,7-Carbonate

12-Chlorodesacetylforskolin 1,9:6,7-dicarbonate of Example 1(b) (0.210 g, 0.461 mmole) was dissolved in 4 ml of THF and then 2 ml of saturated aqueous NaHCO$_3$ solution was added. The reaction mixture was stirred overnight (about 16 hours) and then distributed between ether and H$_2$O. The organic phase was dried and evaporated and then purified by flash chromatography (5% ethyl acetate-CH$_2$Cl$_2$). Evaporation of the product containing fractions gave 0.143 g (72%) of product. Recrystallization from benzene-pentane yielded 12-chlorodesacetylforskolin 6,7-carbonate (analytically pure).

| ANALYSIS: | | |
|---|---|---|
| Calculated for C$_{21}$H$_{29}$ClO$_7$: | 58.80% C | 6.82% H |
| Found: | 58.61% C | 6.83% H |

It is anticipated that the resultant 12-chloroforskolin 6,7-carbonate can be employed, using a procedure analogous to that of Example 1(c) to obtain 12-chlorodesacetylforskolin.

EXAMPLE 10

12-Bromo-7-(2,3-dihydroxypropionyl)desacetylforskolin (Diastereomer A)

The acetonide (0.350 g, 0.608 mmole) of Example 7 was stirred for two days in a solution composed of 5 ml of 80% aqueous acetic acid and 1 ml of methanol. At the end of this time the reaction mixture was distributed between ether and H$_2$O, and then the organic phase was washed with NaHCO$_3$ solution. The residue that remained upon evaporation of the organic phase was purified by flash chromatography (50% ethyl acetate-hexane) to give unreacted starting material and product as a mixture of diastereomers. The recovered starting material was resubjected to the conditions of the hydrolysis for an additional three days and then worked up as before. Flash chromatography of the combined products from the two runs separated the diastereomers when ether was used as an eluent. The fractions containing the fast running isomer (diastereomer A) were combined, evaporated and crystallized from ether-pentane to give 0.0937 g (29%) of 12-bromo-7-(2,3-dihydroxypropionyl)desacetylforskolin (diastereomer A) mp 185°–187° C.

| ANALYSIS: | | |
|---|---|---|
| Calculated for C$_{23}$H$_{35}$BrO$_9$: | 51.59% C | 6.59% H |
| Found: | 51.78% C | 6.63% H |

EXAMPLE 11

12-Bromo-7-(2,3-dihydroxypropionyl)desacetylforskolin (Diastereomer B)

The acetonide (0.350 g, 0.609 mmole) of Example 7 was stirred for two days in a solution composed of 5 ml of 80% aqueous acetic acid and 1 ml of methanol. At the end of this time the reaction mixture was distributed between ether and H$_2$O, and then the organic phase was washed with NaHCO$_3$ solution. The residue that remained upon evaporation of the organic phase was purified by flash chromatography (50% ethylacetate-hexane) to give unreacted starting material and product as a mixture of diastereomers. The recovered starting material was resubjected to the conditions of the hydrolysis for an additional three days and then worked up as before. Flash chromatography of the combined products from the two runs separated the diastereomers when ether was used as eluent. The fractions containing the slow running isomer (diastereomer B) were combined, evaporated and crystallized from benzene-pentane to give 0.0720 g (22%) of 12-bromo-7-(2,3-dihydroxypropionyl)desacetylforskolin (diastereomer B) mp 127°–130 ° C.

| ANALYSIS: | | |
|---|---|---|
| Calculated for C$_{23}$H$_{35}$BrO$_9$: | 51.59% C | 6.59% H |
| Found: | 51.31% C | 6.66% H |

EXAMPLE 12

(a) 12-Fluorodesacetylforskolin 6,7-carbonate

Forskolin 1,9:6,7-dicarbonate (1.60 g, 3.80 mmole) was dissolved in 45 ml. of dry THF and then 4.5 mL of 1M lithium bis[trimethylsilyl]amide was added. The reaction mixture was stirred at room temperature for 30 minutes and then the solvent was removed under reduced pressure and the residue re-dissolved in 40 mL of dry THF. This solution of the lithium enolate was added rapidly to a solution of acetyl hypofluorite, prepared in the following manner: To 8.2 g of sodium acetate (0.1 mole) was added 6.0 g of glacial acetic acid (0.1 mole). The slurry was mixed well with a spatula and allowed to stand with occasional stirring until a uniform, free-flowing powder was obtained. This was then suspended in CFCl$_3$ (450 mL) at −70° C. and a mixture of fluorine in nitrogen (20%) was introduced slowly through a fritted glass inlet. After 30 minutes, addition of an aliquot to acidic aqueous KI indicated an oxidizing solution. After the addition of the lithium enolate, the solution was stirred for 5 minutes in the cold and then quenched with 400 mL of 5% sodium thiosulfate solution. The aqueous phase was separated and the organic phase was washed further with NaHCO$_3$ solution and then water. After drying and evaporating the organic phase the residue was treated for 90 minutes with a 1:1 solution of saturated NaHCO$_3$ solution and THF, to give conversion to the more easily separable 6,7-monocarbonate. The reaction mixture was distributed between ether and H$_2$O, and then the residue obtained from the dried and evaporated organic phase was purified by flash chromatography (3% ethyl acetate-CH$_2$Cl$_2$). Combination of the product containing fractions gave 0.2109 g (13%) of product. Recrystallization from ether-pentane, yielded 12-fluorodesacetylforskolin 6,7-carbonate, m.p. 223°–225° C.

ANALYSIS:

| Calculated for C$_{21}$H$_{29}$FO$_7$: | 61.16% C | 7.09% H |
|---|---|---|
| Found: | 61.21% C | 7.25% H |

(b) 12-Fluorodesacetylforskolin

12-Fluorodesacetylforskolin 6,7-carbonate of Example 12(a) (0.190 g, 0.46 mmole) was stirred for 1 hour in 2 mL of K$_2$CO$_3$/methanol/H$_2$O. At the end of this time it was distributed between CH$_2$Cl$_2$ and H$_2$O and then the residue obtained from the organic phase was purified by flash chromatography (25% ethyl acetate-CH$_2$Cl$_2$). The product containing fractions were combined and recrystallized from methanol-H$_2$) to give 0.061 g (34%) of 12-fluorodesacetylforskolin, mp 183°–184° C.

ANALYSIS:

| Calculated for C$_{20}$H$_{21}$FO$_6$: | 62.16% C | 8.09% H |
|---|---|---|
| Found: | 61.96% C | 7.94% H |

EXAMPLE 13

12-Fluoroforskolin 12-fluorodesacetylforskolin of Example 12(b) (0.3257 g, 0.843 mmole) was dissolved in 5 mL of pyridine and then acetic anhydride (0.125 mL, 0.135 g, 1.32 mmole) was added. The reacting mixture was stirred for 48 hours and then distributed between ether and H$_2$O. The aqueous phase was separated and the organic phase was washed once with H$_2$O and once with 5% HCl. The residue obtained from the dried and evaporated organic phase was purified by flash chromatography (5% ethyl acetate-CH$_2$Cl$_2$). Combination and evaporation of the product containing fractions gave 0.1272 g (35%) of product. Recrystallization from CH$_2$Cl$_2$-pentane yielded 12-fluoroforskolin, m.p. 263°–265° C.

ANALYSIS:

| Calculated for C$_{22}$H$_{33}$FO$_7$: | 61.66% C | 7.76% H |
|---|---|---|
| Found: | 61.46% C | 7.79% H |

EXAMPLE 14

(a) 12-Fluorodesacetylforskolin 1,9-dimethylformamide acetal 12-fluorodesacetylforskolin 6,7-carbonate of Example 12(a) (0.6973 g, 1.68 mmole) was stirred for 2 hours at 55° C. in excess dimethylformamide dimethyl acetal. At the end of this time the volatiles were removed under reduced pressure and the residue stirred in methanolic K$_2$CO$_3$. After one hour the reaction mixture was distributed between CH$_2$Cl$_2$ and H$_2$O and then the organic phase was dried, evaporated and purified by flash chromatography (30% ethyl acetate-hexane). Combination of the product-containing fractions gave 0.342 g (46%) of product. Recrystallization from methanol-H$_2$O yielded 12-fluorodesacetylforskolin 1,9-dimethylformamide acetal, mp 179°–181° C.

ANALYSIS:

| Calculated for C$_{23}$H$_{36}$FNO$_6$: | 62.56% C | 8.22% H | 3.17% N |
|---|---|---|---|
| Found: | 62.69% C | 8.34% H | 3.05% N |

(b) 12-fluoro-7-(N-methylaminocarbonyl)desacetylforskolin 1,9-dimethylformamide acetal 12-Fluorodesacetylforskolin 1,9-dimethylformamide acetal of Example 14(a) (0.3418 g, 0.774 mmole) was dissolved in 30 mL of dry THF to which was then added 0.077 mL of 1M lithium bis(trimethylsilyl)amide (0.077 mmole) and 0.047 mL (0.046 g, 0.80 mmole) of methyl isocyanate. The reaction mixture was refluxed for 2 hours and then quenched by the addition of 0.20 mL H$_2$O. Evaporation gave a residue that was chromatographed (50% ethyl acetate-hexane) to give, after combination and evaporation of the appropriate fractions, 0.230 g (60%) of product. Recrystallization from ether-pentane yielded mp 204°–205° C.

ANALYSIS:

| Calculated for C$_{25}$H$_{39}$FN$_2$O$_7$: | 60.22% C | 7.88% H | 5.62% N |
|---|---|---|---|
| Found: | 60.14% C | 8.29% H | 5.72% N |

(c) 12-fluoro-7-(N-methylaminocarbonyl)desacetylforskolin 12-fluoro-7-(N-methylaminocarbonyldesacetylforskolin 1,9-dimethylformamide acetal of Example 14(b) (0.1874 g, 0.376 mmole) was stirred overnight in 10 mL of 1:1 80% aqueous acetic acid:methanol. At the end of this time the reaction was distributed between H$_2$O and CH$_2$Cl$_2$ and the organic phase was separated and washed with NaHCO$_3$ solution. The residue obtained from the evaporation of the organic phase was purified by flash chromatography (20% ethyl acetate-CH$_2$Cl$_2$). The product-containing fractions were combined and recrystallized from ether-pentane and then from methanol-H$_2$O to give 0.0831 g of 12-fluoro-7-(N-methylaminocarbonyl)desacetylforskolin (49.7%), mp 149°–150° C.

ANALYSIS:

| Calculated for C$_{22}$H$_{34}$FNO$_7$: | 59.58% C | 7.73% H | 3.16% N |
|---|---|---|---|

-continued

ANALYSIS:

Found: 59.82% C  7.86% H  2.69% N

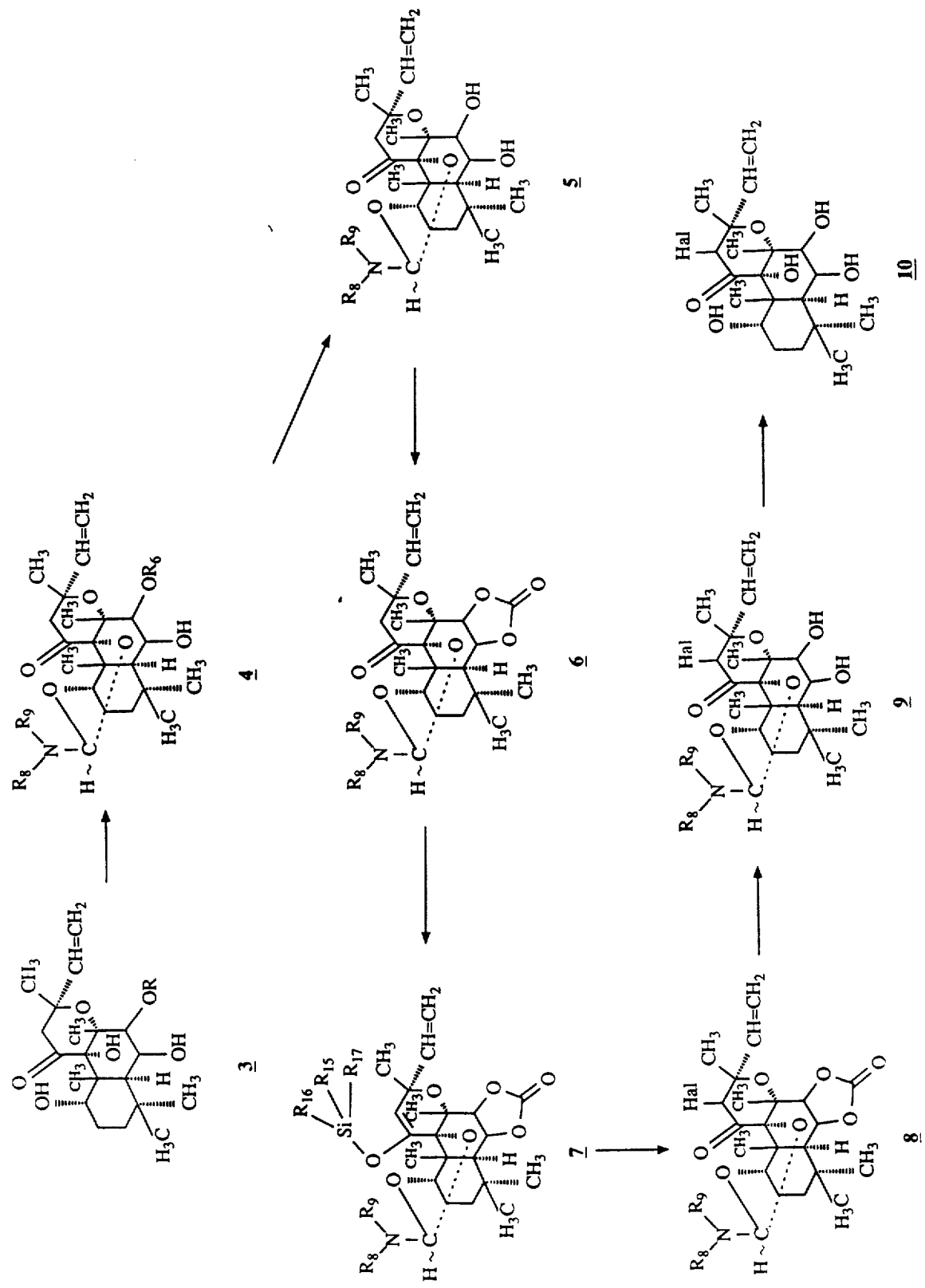

REACTION SCHEME B
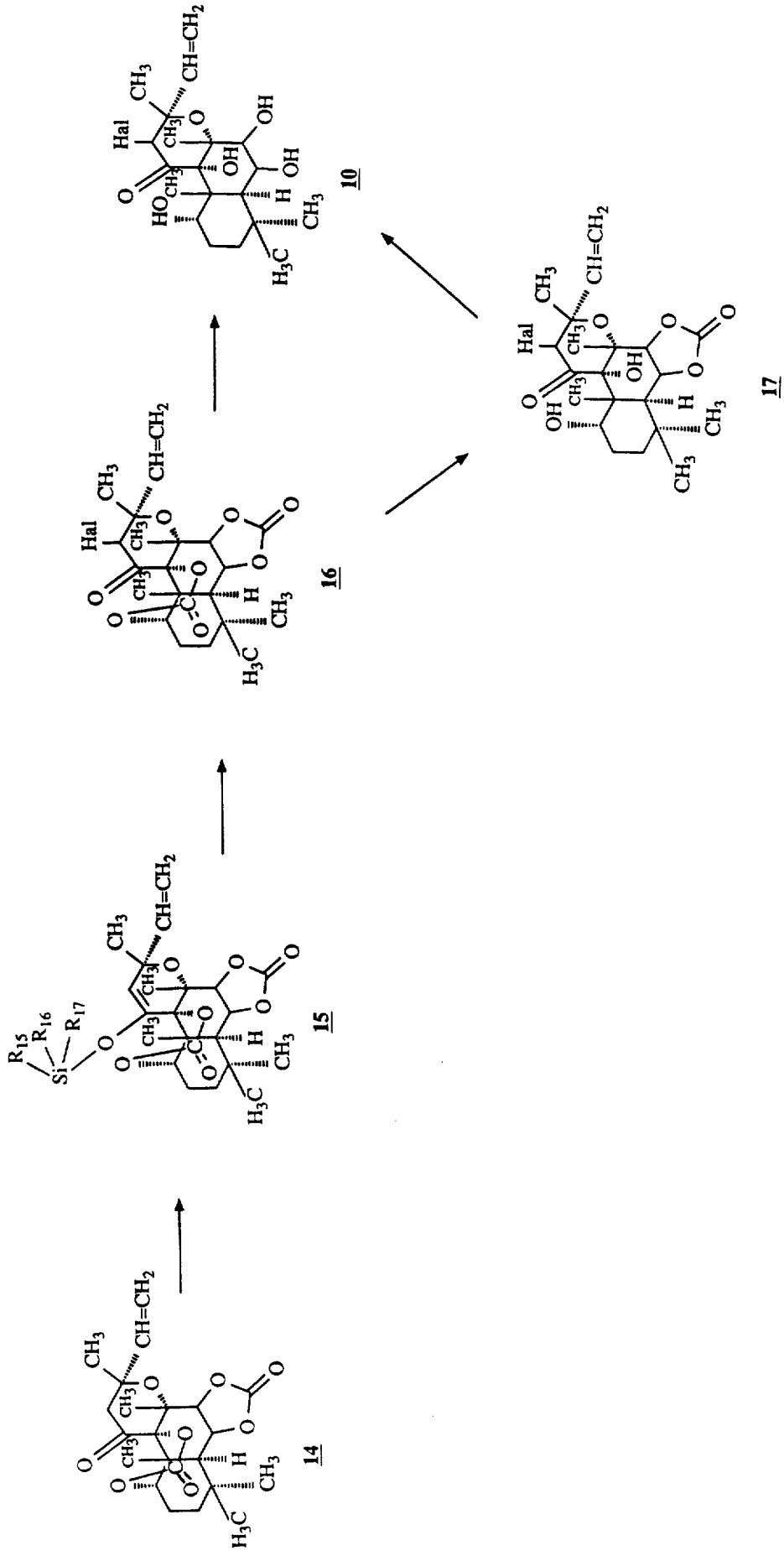

I claim:

1. A compound of the formula

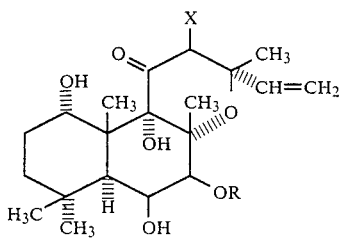

wherein X is F, Cl, Br or I: R is hydrogen or

where $R_1$ is a lower alkyl, or an optical or geometric isomer thereof.

2. The compound as defined in claim 1 wherein X is F or I.

3. The compound as defined in claim 1 wherein X is Cl or Br.

4. The compound as defined in claim 1 wherein R is hydrogen.

5. The compound as defined in claim 1 which is 12-chlorodesacetylforskolin.

6. The compound as defined in claim 1 which is 12-chloroforskolin.

7. The compound as defined in claim 1 which is 12-bromodesacetylforskolin.

8. The compound as defined in claim 1 which is 12-bromoforskolin.

9. The compound as defined in claim 1 which is 12-fluorodesacetylforskolin.

10. The compound as defined in claim 1 which is 12-fluoroforskolin.

11. An intraocular pressure reducing composition comprising an inert adjuvant and, as the active ingredient, an amount effective in reducing intraocular pressure of a compound of the formula

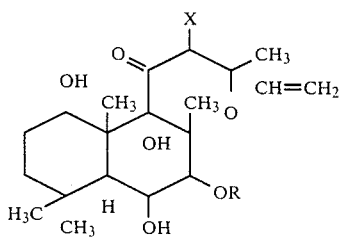

wherein X is F, Cl, Br or I; R is hydrogen or

where $R_1$ is a lower alkyl, or an optical or geometric isomer thereof.

12. The composition as defined in claim 11 wherein R is hydrogen.

13. The composition as defined in claim 11 wherein said active ingredient is 12-chlorodesacetylforskolin.

14. The composition as defined in claim 11 wherein said active ingredient is 12-chloroforskolin.

15. The composition as defined in claim 11 wherein said active ingredient is 12-bromodesacetylforskolin.

16. The composition as defined in claim 11 wherein said active ingredient is 12-bromodesacetylforskolin.

17. The composition as defined in claim 11 wherein said active ingredient is 12-fluorodesacetylforskolin.

18. The composition as defined in claim 11 wherein said active ingredient is 12-fluoroforskolin.

19. A method of reducing intraocular pressure in mammals comprising administering to a mammal requiring intraocular pressure reduction an intraocular pressure reducing effective amount of a compound of the formula

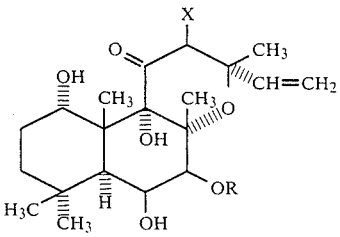

wherein X is F, Cl, Br or I; R is hydrogen or

where $R_1$ is a lower alkyl, or an optical or geometric isomer thereof.

20. The method as defined in claim 19 where R is hydrogen.

21. The method as defined in claim 19 wherein said compound is 12-chlorodesacetylforskolin.

22. The method as defined in claim 19 wherein said compound is 12-chloroforskolin.

23. The method as defined in claim 19 wherein said compound is 12-bromodesacetylforskolin.

24. The method as defined in claim 19 wherein said compound is 12-bromoforskolin.

25. The method as defined in claim 19 wherein said compound is 12-fluorodesacetylforskolin.

26. The method as defined in claim 19 wherein said compound is 12-fluoroforskolin.

* * * * *

UNITED STATES PATENT AND TRADEMARK OFFICE
CERTIFICATE OF CORRECTION

PATENT NO. : 4,871,764

DATED : October 3, 1989

INVENTOR(S) : Gregory Michael Shutske

It is certified that error appears in the above-identified patent and that said Letters Patent is hereby corrected as shown below:

Column 17, line 5, insert Reaction Scheme A and Reaction Scheme B as per attached sheets.

Signed and Sealed this

First Day of January, 1991

*Attest:*

HARRY F. MANBECK, JR.

*Attesting Officer*    *Commissioner of Patents and Trademarks*